(12) United States Patent
Yilmaz et al.

(10) Patent No.: US 6,876,444 B2
(45) Date of Patent: Apr. 5, 2005

(54) REFRACTOMETER

(75) Inventors: Sükrü Yilmaz, Berlin (DE); Mathis Kuchejda, Berlin (DE)

(73) Assignee: Franz Schmidt & Haensch GmbH & Co., Berlin (DE)

( * ) Notice: Subject to any disclaimer, the term of this patent is extended or adjusted under 35 U.S.C. 154(b) by 86 days.

(21) Appl. No.: 10/276,651

(22) PCT Filed: May 18, 2001

(86) PCT No.: PCT/DE01/01992
§ 371 (c)(1),
(2), (4) Date: Dec. 17, 2002

(87) PCT Pub. No.: WO01/88506
PCT Pub. Date: Nov. 22, 2001

(65) Prior Publication Data
US 2003/0156278 A1 Aug. 21, 2003

(30) Foreign Application Priority Data
May 19, 2000 (DE) .......................... 100 25 789

(51) Int. Cl.[7] ............................................. G01N 21/41
(52) U.S. Cl. ....................................... 356/135; 356/136
(58) Field of Search ................................ 356/135–136, 356/445

(56) References Cited

U.S. PATENT DOCUMENTS

| | | | | |
|---|---|---|---|---|
| 4,699,511 A | * | 10/1987 | Seaver | 356/136 |
| 5,822,073 A | * | 10/1998 | Yee et al. | 356/445 |
| 6,376,829 B1 | * | 4/2002 | Okugawa | 250/225 |
| 6,738,141 B1 | * | 5/2004 | Thirstrup | 356/445 |

FOREIGN PATENT DOCUMENTS

| | | | | |
|---|---|---|---|---|
| WO | WO 93/14392 | * | 7/1993 | G01N/21/55 |

* cited by examiner

Primary Examiner—Zandra Smith
Assistant Examiner—Kara Geisel
(74) Attorney, Agent, or Firm—Cohen, Pontani, Lieberman & Pavane

(57) ABSTRACT

A refractometer with a measuring prism on whose measuring surface a sample to be tested can be mounted, which sample can be illuminated by a light beam emitted by a source of light under a range of angles that includes a critical angle for total reflection, and with a reciever for recieving the reflected light. An optical device that decomposes the reflected light into a color spectrum that is mounted in the path of the reflected light between the measuring surface and the reciever.

3 Claims, 1 Drawing Sheet

REFRACTOMETER

PRIORITY CLAIM

This is a U.S. national stage of application No. PCT/DE01/01992, filed on 18 May 2001. Priority is claimed on that application and on the following application: Country: Germany, Application No.: 100 25 789.5, Filed: 19 May 2000.

BACKGROUND OF THE INVENTION

1. Field of the Invention

The invention concerns a refractometer with a measuring prism on whose measuring surface a sample to be tested can be mounted. The sample can be illuminated by a light beam emitted by a source of white light under a range of angles that includes the critical angle for total reflection. The refractometer also has a receiver for receiving the reflected light.

2. Description of the Related Art

Refractometers are used to measure the index of refraction of solid, liquid, or gaseous substances. In total reflectometers, such as the Abbe refractometer, the critical angle of the total reflection is determined with the use of a measuring prism of known index of refraction, which is brought into optical contact with the substance to be tested.

These refractometers operate with white light, because the effect of dispersion can be compensated by rotation of two direct-vision prisms in the observation telescope.

SUMMARY OF THE INVENTION

The goal of the invention is to develop simple means of improving a refractometer, e.g., the Abbe refractometer, with respect to its ability to provide information about a substance to be tested.

In accordance with the invention, this goal is achieved by mounting an optical device that decomposes the reflected light into a color spectrum in the path of the reflected light between the measuring surface and the receiver.

In this solution to the problem, the dispersion that occurs is not eliminated again by an oppositely acting prism, but rather the color spectrum can be utilized to produce intensity curves for various wavelengths. If a two-dimensional diode array is used for detection, then the columns correspond to the various wavelengths, and the position of the light-dark border within the individual columns depends on the index of refraction at the given wavelength. The index of refraction can thus be represented as a function of the wavelength.

The use of the CCD array provides still another advantage.

Due to the total reflection, a number of rows will always be light, namely, those on which the totally reflected light is incident. However, this light now contains information about the absorption of the sample, which likewise can be analyzed.

DESCRIPTION OF THE PRESENTLY PREFERRED EMBODIMENTS

Figure 1:
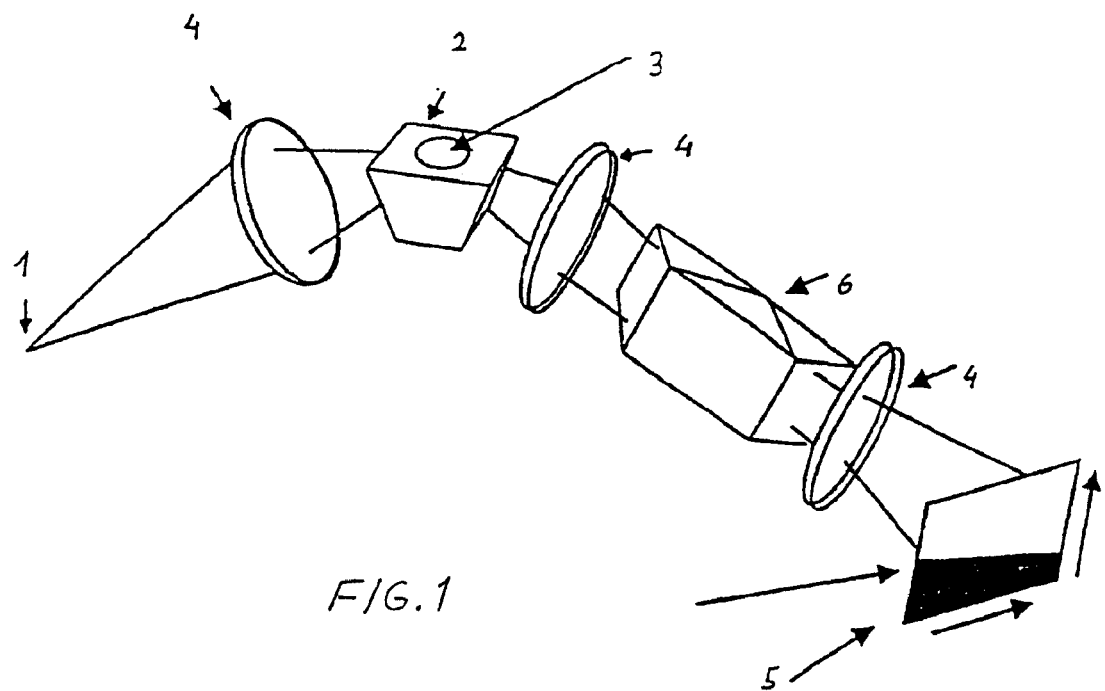
FIG. 1 is a diagrammatic perspective view of a refractor according to the invention.

FIG. 1 shows the design of the refractometer in simplified form with the source of white light 1, the measuring prism 2, and the sample 3 on the measuring surface of the prism. The systems of lenses 4 are merely indicated in the drawing. An optical device 6 that produces a spectrum, e.g., a grating or a direct-vision prism, is arranged between the measuring prism and the receiver 5.

The receiver may be a two-dimensional CCD array, or a one dimensional CCD array which is moved by stepper motors parallel to the columns (along the color bands). In this way, although the measurement can only be made sequentially with respect to time, a longer row of correspondingly greater resolution for the index of refraction and wavelength determination is provided.

Figure 2:
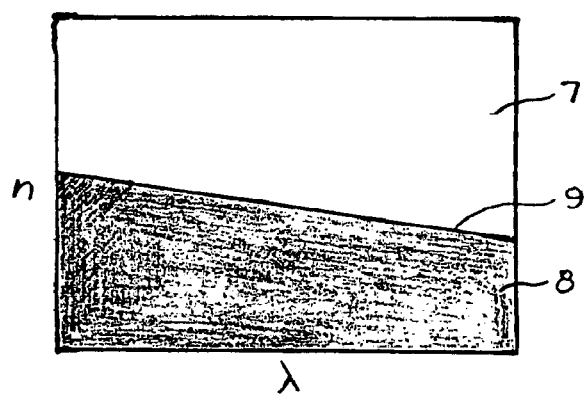
FIG. 2 is a graphic representation of the light and dark areas on the CCD array.

FIG. 2 shows the two-dimensional CCD array wherein the border 9 between light area 7 and dark area 8 represents a plot of the index of refraction n as a function of wavelength $\lambda$.

What is claimed is:

1. A refractometer comprising:

a light source which emits a beam of white light;

a measuring prism having a measuring surface on which a sample to be tested can be mounted, said measuring surface being arranged to receive said beam of white light in a range of angles including the critical angle of total reflection so that said measuring prism transmits a reflected light beam along a path;

an optical device that decomposes the reflected light beam transmitted by said measuring prism into a color spectrum, said optical device being mounted in the path of the reflected light beam; and a receiver comprising a two-dimensional CCD array which receives said color spectrum, said spectrum producing on the CCD array a light area and a dark area having a border which represents the index of refraction of the sample.

2. A refractometer as in claim 1 wherein the optical device is a grating.

3. A refractometer as in claim 1 wherein the optical device is a dispersion prism.

* * * * *